US00RE39006E

(19) United States
(12) Reissued Patent
Houwen et al.

(10) Patent Number: US RE39,006 E
(45) Date of Reissued Patent: Mar. 7, 2006

(54) METHOD OF DETECTING HEMATOPOIETIC PROGENITOR CELLS

(75) Inventors: Berend Houwen, Redlands, CA (US); Yukio Tsujino, Hyogo-ken (JP); Takashi Morikawa, Hyogo-ken (JP); Yoshiro Ikeuchi, Hyogo-ken (JP); Yukio Hamaguchi, Hyogo-ken (JP); Fu-sheng Wang, Hyogo (JP); Kojiro Hirai, Hyogo (JP)

(73) Assignee: Sysmex Corporation, Kobe (JP)

(21) Appl. No.: 10/704,463

(22) Filed: Nov. 7, 2003

Related U.S. Patent Documents

Reissue of:
(64) Patent No.: 5,830,701
Issued: Nov. 3, 1998
Appl. No.: 08/829,239
Filed: Mar. 28, 1997

(51) Int. Cl.
*C12Q 1/04* (2006.01)

(52) U.S. Cl. ..... 435/29; 435/4; 435/34; 435/325; 435/366; 435/372; 436/164; 436/172

(58) Field of Classification Search ..... 435/29, 435/34, 4, 325, 366, 372; 436/164, 172
See application file for complete search history.

(56) References Cited

U.S. PATENT DOCUMENTS 5,413,938 A * 5/1995 Tsujino et al.
5,538,893 A * 7/1996 Sakata et al.

OTHER PUBLICATIONS

Atzpodien et al., "Human Bone Marrow CFU–GM & BFU–E Localized by Light Scatter Cell Sorting," Exp. Cell Biol. 55 (5) 265–270, 1987.*

Lebeck, L. K. et al., "Peripheral Blood Stem Cell Harvests: Laboratory Indicators for the timing of Apheresis procedures," International Society for Laboratory Hematology, vol. 1, No. 1, p. 62, 1995.

Takekawa, K. et al., "A New Method of Identification of Peripheral Blood CD 34 Positive Fraction with Automated Blood Corpuscle Counter (SE–9000™)," The Japanese Journal of Clinical Hematology, vol. 36, No. 9, 1995.

Takekawa, K. et al., "Identification of Hematopoietic Stem Cells by the SE–9000™ Automated Hematology Analyzer in Peripheral Blood Stem Cell Harvesting Samples," Journal, of the American Society of Hematology, vol. 88, No. 10, Supplement 1, 250b, 1996.

Yamada, H. et al., "On the Timing of Sample Peripheral blood Stem Cells Through SE–9000™ IMI Channels." Japanese Journal of Medical Technology, vol. 145, No. 3, p. 501, 1996.

Mougi, H. et al., "Determination of the Time of Peripheral Blood Stem Cell Harvest Using an Automatic Cell Analyzer," Med. J. Kagoshima Univ., vol. 48, No. 2, p. 139–146, 1996.

Houwen, B. et al., "The Timing of Peripheral Blood Stem Cell Harvests: Screening for Hematopoietic Stem Cells on the SE–9000," International Society for Laboratory Hematology, vol. 2, No. 2, p. 51, 1996.

Takekawa, K. et al., "Detection of Hematopoietic Stem Cells Using Automated Blood Cell Counter and Flow Cytometry," The Japanese Journal of Clinical Pathology, Special Extra No. 99, 1995.

Takekawa, K et al., "Possibility of Identification of Hematopoietic Stem Cells Using Conventional Blood Cells Counter," Eur J Hemalton, 55:207–208, 1995.

* cited by examiner

*Primary Examiner*—Leon B. Lankford, Jr.
(74) *Attorney, Agent, or Firm*—Brinks Hofer Gilson & Lione

(57) ABSTRACT

Improved method for detecting and/or counting the appearance of hematopoietic progenitor cells which comprises the steps of mixing a blood sample with a reagent capable of detecting immature cells without employing any immunological techniques, obtaining cell information about the thus treated sample using a particle analyzer and constructing a cell distribution profile, delineating a portion of the profile as a zone in which at least one subclass of hematopoietic progenitor cells appear, and counting the cells within the zone. The method is capable of detecting the appearance of hematopoietic progenitor cells in a simple and positive manner.

12 Claims, 5 Drawing Sheets

CD34 POSITIVE SELECTION
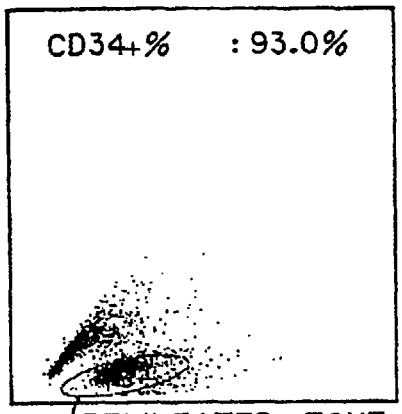
Fig. 1
Fig. 2
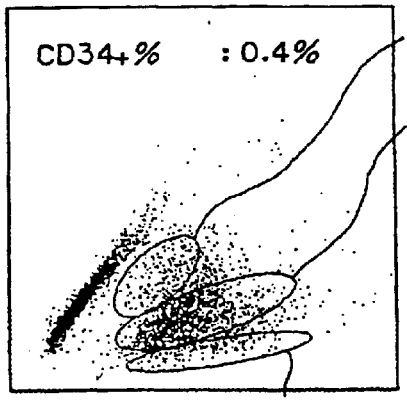
| MANUAL 200 COUNT DATA | |
|---|---|
| METAMYELOCYTE | 4% |
| MYELOCYTE | 5% |
| PROMYELOCYTE | 1% |
| MYELOBLAST | 1% |
Fig. 3
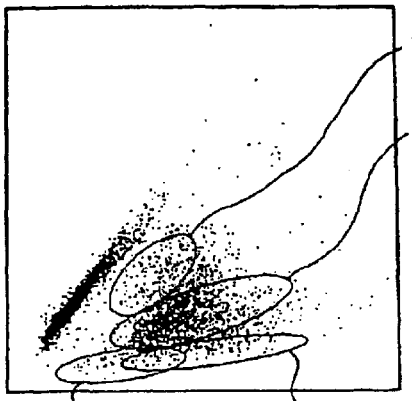
| | |
|---|---|
| CD34+% | : 40/μL |
| IMI TOTAL | : 520/μL |
| CELL COUNT IN DELINEATED ZONE | : 60/μL |

METHOD OF DETECTING HEMATOPOIETIC PROGENITOR CELLS

Matter enclosed in heavy brackets [ ] appears in the original patent but forms no part of this reissue specification; matter printed in italics indicates the additions made by reissue.

BACKGROUND OF THE INVENTION

This invention relates to a method of detecting hematopoietic progenitor cells (HPCs). The method is capable of simple counting of peripheral blood HPCs for use as transplants in PBSCT (peripheral blood stem cell or PBSC transplantation) and it provides a useful index for determining the right time to collect PBSCs. PBSCs are the most primitive fraction of HPCs and are considered the "origin" or stem cells of all hematopoiesis. As will be explained specifically below, the term "hematopoietic progenitor cells" as used herein is synonymous with but broader in sense than the term "peripheral blood stem cells".

Bone marrow transplantation (BMT) has seen a substantial development over the past 30 years as the last resort in the treatment of malignant diseases such as leukemia, lymphoma, myeloma and certain solid tumors. In spite of the many advantages it has, BMT also involves various difficulties such as the need to perform multiple bone marrow apheresis while patient or donors are under on general anesthesia. Hence, the feasibility of this technique is limited to either university hospitals or other major medical institutions of a comparable class and there exist many hospitals that do not practice BMT.

On the other hand, the recent advances in the studies of hematopoietic stem cells and the introduction of pharmaceutical preparations containing hematopoietic factors as an active ingredient have made it possible to mobilize HPCs within the peripheral blood. This, combined with the remarkable improvements in the technology of blood component separators, has contributed to the rapidly increasing use of PBSCT.

BMT and PBSCT share the common feature of transplanting stem cells but PBSCT has the following advantages over BMT:

(1) the donor need not be placed under general anesthesia when extracting stem cells but simple apheresis will suffice, which contributes to safety;

(2) more rapid hematopoietic recovery when compared with BMT is possible after the transplantation and, hence, the risk of infection and the need for blood transfusions is reduced;

(3) the period of hospitalization is shortened;

(4) a large number of stem cells are included in the transplant;

(5) contamination by tumor cells is limited; and (6) the incidence of death associated with the transplatation is low.

The general procedure of PBSCT is as follows. First, the patient is administered chemotherapy, hematopoietic growth hormones (interleukins e.g. granulocyte colony stimulating factor (G-CSF)) and any other necessary reagents, whereupon the leukocyte count in the peripheral blood initially decreases while on the subsequent day 5–7 or later, the leukocyte count starts to increase. Similarly, but not necessarily concurrently with this event, the number of hematopoietic stem cells also increases.

When a sufficiently large number of hematopoietic stem cells have been mobilized in the peripheral blood (usually in about 5–20 days), the stem cells are collected by means of a blood component separator and stored frozen. In this instance, it is necessary to know exactly when the number of stem cells in the peripheral blood is increased. The timing of mobilization and collecting of the hematopoietic stem cells should be neither too early nor too late in order to secure an adequate number of stem cells.

In the next step, the cancer cells are killed by applying very high levels of chemotherapy and/or radiotherapy that are sufficient to destroy the patient's bone marrow. Thereafter, the previously collected stem cells are transplanted so as to achieve rapid recovery of the hematopoietic capability of the patient.

As will be understood from the foregoing, successful PBSCT requires efficient collection of hematopoietic cells and, to this end, the mobilization of peripheral stem cells has to be monitored correctly. Two common methods currently used to count stem cells are a colony assay method and a CD34 positive (a marker which is present on the cell surface of HPC) cell count method using flow cytometry (FCM). In the colony assay method, the number of stem cells to be collected is adjusted appropriately in a suitable culture medium such as IMDM and cultivation is performed in a blood stem cell assay medium for 14 days in a $CO_2$ incubator while a colony count is obtained with a phase-contrast microscope. In the CD34 positive cell count method using FCM, particularly in single-color analysis, a whole blood sample is reacted with a fluorescence-labelled anti-CD34 monoclonal antibody and, after hemolysis flow cytometry is performed and a CD34 positive cell count is obtained from a scattergram of lateral scattered light and flourescence or a histogram of fluorescence. In a two-color analysis, flow cytometry is performed using an anti-CD34 monoclonal antibody and an anti-CD45 monoclonal antibody and the CD45 positive cells alone are first incorporated as data, which are then analyzed using lateral scattered light and CD34 fluorescence as parameters such that cells are counted which produce low levels of lateral scattered light and which express CD34.

The colony assay method is the currently the most accurate way to obtain the correct PBSC count and this is sometimes used to perform the stem cell count on samples that have been subjected to apheresis. A problem with this method is the long time (2 weeks) that is required to complete the measurement and, therefore, it is not suitable to determine the right timing for HPC/PBSCs collection. In addition, while requiring a high level of skill on the part of the operating personnel, the colony assay method is not a technique that assures good reproduction of the results and which can be adopted in routine work. High operating cost is another problem with this method.

Compared to the colony assay method, the CD34 positive cell count method can be completed in a short time but it still takes at least 1–2 hours in the counting procedure. For monitoring the mobilization of stem cells within the peripheral blood, the measurement is ideally continued for 3–5 days or more. However, using a flow cytometer in order to count CD34 positive cells, the method under consideration is difficult to adopt as a routine technique on account of the high cost of equipment and reagents, as well as the scarcity of skilled engineers. In addition, gating is necessary to determine specific cell zones on a scattergram or histogram and this produces considerable differences from one facility to another.

Given these circumstances, a blood cell count is often adopted in clinical practice and the degree of mobilization of HPC is monitored indirectly by looking at the pattern of increase in the number of leukocytes and platelets and the right time to collect stem cells is determined on the basis of these results, assuming a state of mobilization of HPC. Some people argue that this method suffcies for clinical purposes but it is obvious from many observation that the method lacks consistency. Stated more specifically, if the leukocyte count increases in synchronism with the platelet count, sometimes this helps to determine the right time to collect HPC; however, this is often not the case, especially if there is a mismatch between the rates of increase of the two counts.

Recently, an automatic blood cell analyzer equipped with channels capable of detecting immature leukocytes (IMI, or immature leukocyte information, channel) has been introduced into the market as Model SE-9000 from Toa Medical Electronics Co., Ltd. and many reports were thereafter published on the results of PBSC counting using this model; examples are as follows: Lebeck, L. K. et al., International Society for Laboratory Hematology, Vol.1, No.1, p.62, 1995; Takekawa, K. et al., The Japanese Journal of Clinical Hematology, Vol.36, No.9, 1995; Yamada, H. et al., Japanese Journal of Medical Technology, Vol.145, No.3, p.501, 1996; Mougi, H. et al., Med. J. Kagoshima Univ., Vol.48, No.2, p.139–146, 1996; Houwen, B. et al., International Society for Laboratory Hematology, Vol.2, No.2, p.51, 1996; and Takekawa, K. et al., Journal, of the American Society of Hematology, Vol.88, No.10, Supplement 1, 250b, 1996. According to these reports, a statistically significant correlationship has been found to exist between the total count of immature leukocytes (IMI total) and the number of CD34 positive cells as determined with a flow cytometer.

In fact, however, the IMI total includes the cells that appear in the zones for blasts, immature granulocytes and left shifts and the PBSC count is not the only parameter that is reflected by the IMI total. In other words, the IMI total which includes the above-mentioned rather mature juvenile leukocytes involves such substantial errors that it is not suitable for use in monitoring the appearance of PBSCs that can be adopted in PBSCT.

SUMMARY OF THE INVENTION

The present invention has been accomplished under these circumstances and has as its objective to provide a method which is capable of detecting the appearance of HPCs in a simple manner.

The stated object of the invention can be attained by a method for detecting and/or counting the appearances of hematopoietic progenitor cells, which comprises the steps of:

- mixing a blood sample with a reagent capable of detecting immature cells without employing any immunological techniques;
- obtaining cell information about the thus treated blood sample using a particle analyzer and constructing a cell distribution profile;
- delineating a portion of said profile as a zone in which at least one subclass of hematopoietic progenitor cells appear; and
- counting the cells within said zone.

BRIEF DESCRIPTION OF THE DRAWINGS

FIG. 1. is a cell distribution profile constructed by SE-9000 measurement of the samples prepared by the method described in Example 1;

FIG. 2 is a cell distribution profile constructed by SE-9000 measurement of peripheral blood samples in which HPCs were immobilized;

FIG. 3 is a cell distribution profile constructed by SE-9000 measurement of PBSC-mobilized peripheral blood samples within the zone of a scattergram which was delineated by the method of the invention:

DETAILED DESCRIPTION OF THE INVENTION

The term "hematopoietic progenitor cells (HPCs)" as used herein refers collectively to those cells which are yet to reach the stage of blasts in the process of differentiation of pluripotent stem cells into various lineages of blood cells and is broader in a sense in that it contains than the term "peripheral blood stem cells (PBSCs), but also more developed precursor or progenitor cells.

Figure 9:
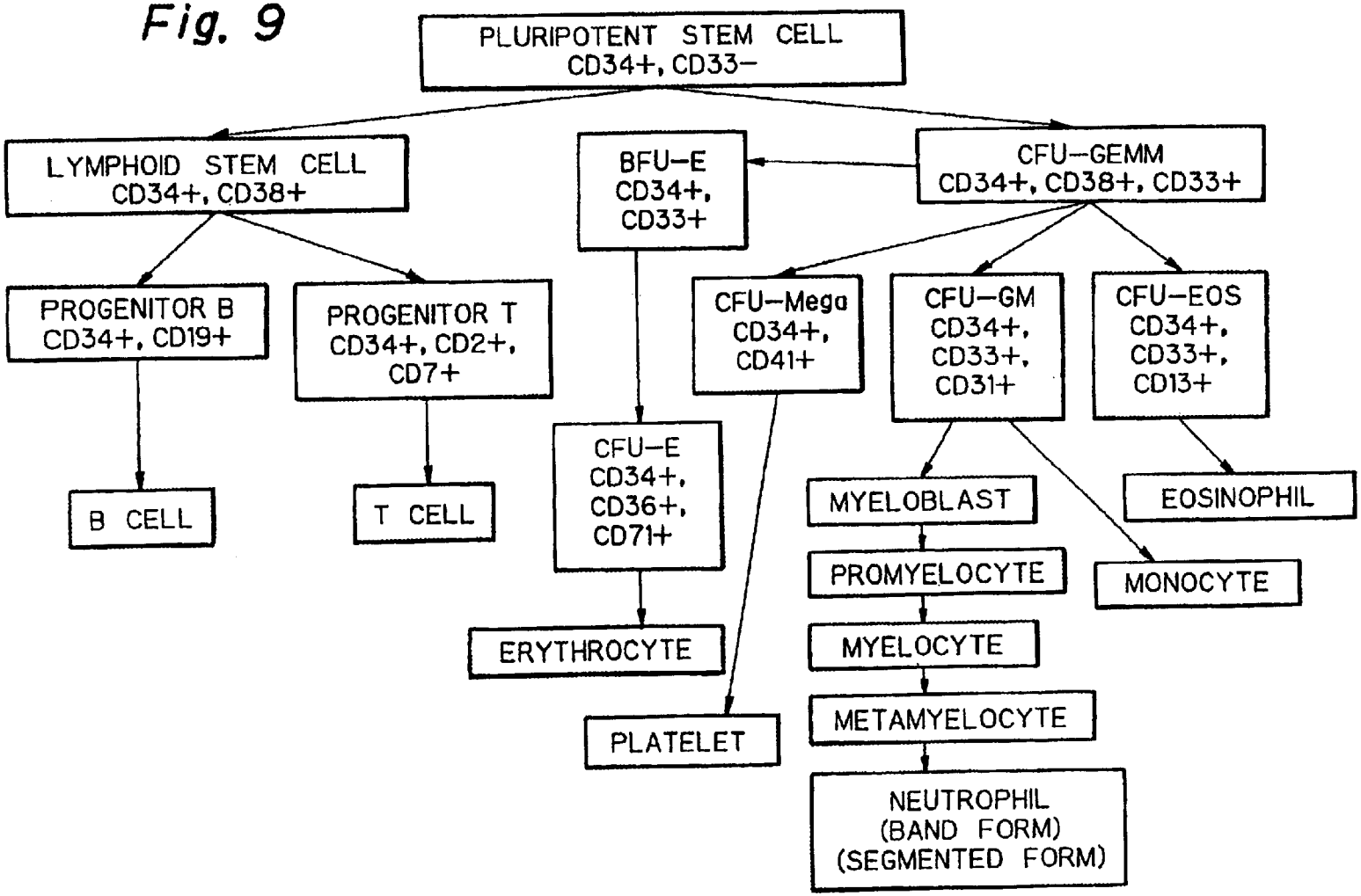
FIG. 9 is a chart illustrating the process of corpuscular differentiation and the relationship between each subclass of HPCs and the associated surface antigen.

Hematopoietic progenitor cells (HPCs) consist of many subclasses including pluripotent stem cells, lymphoid stem cells, CFU-GEMM colony forming unitgranulocyte/erythroid/macrophage/megakaryocyte, BFU-E, CFU-E, CFU-Meg, CFU-GM colony forming unitgranulocyte/macrophage, CFU-EoS colony forming uniteosinophil, progenitor B cells and progenitor T cells (see FIG. 9).

A reagent capable of detecting immature cells is used in the invention and taking, as an example, the case of granulocytes (i.e., neutrophils, eosinophils and basophils), the term "immature cells" refers collectively to those cells which are yet to reach the stage of mature cells in the process of differentiation of hematopoietic progenitor cells into mature cells by passing through the following successive stages: (myeloblasts→promyelocytes→myelocytes→metamyelocytes→band cells→segmented cells). The process of differentiation shown in FIG. 9 refers only to neutrophils and the illustration of eosinophils and basophils is omitted.

The term "a reagent capable of detecting immature cells without employing any immunological techniques" as used herein refers to those reagents which are capable of detecting immature cells without employing any immunological reactions that take place between one of the cell surface antigens characteristic of the subclasses shown in FIG. 9 and the antibody directed against said antigen (e.g. an anti-CD34 antibody).

A typical example of the reagent to be used in the invention (which is capable of detecting immature cells without employing any immunological techniques) is an aqueous solution containing a water-soluble surfactant that can lyse erythrocytes. A preferred surfactant is nonionic surfactant based on polyoxyethylene (POE). A more preferred example is one having the general formula of $R_1$-$R_2$-

$(CH_2CH_2O)_n$-H where $R_1$ is an alkyl, alkenyl or alkinyl group having 10–25 carbon atoms; $R_2$ is O,

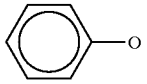

or Coo; and n is an integer of 10–40.

Particularly preferred POE-base nonionic surfaces are those in which $R_1$ is an alkyl, alkenyl or alkinyl group having 10–25 carbon atoms, $R_2$ is O and n is an integer of 10–30, as exemplified by POE(15) oleyl ether, POE(16) oleyl ether, and POE(20) lauryl ether.

The concentration of the nonionic surfactant varies from one surfactant to another; referring to the specific examples just mentioned above, POE(15) oleyl ether may be used at a concentration in the range of 1–9 g/L, preferably 3–7 g/L, POE(16) oleyl ether in the range of 5–50 g/L, preferably 15–35 g/L, and POE(20) lauryl ether in the range of 0.1–2.0 g/L, preferably 0.5–1.5 g/L. Given the same number of carbon atoms in hydrophobic groups, polyoxyethylene-base nonionic surfactants have a greater potential to damage cells as the value of n decreases, and vice versa. Given the same value of n, the cell damaging potential of polyoxyethylene-base nonionic surfactants will increase as the number of carbon atoms in hydrophobic groups decreases. Considering this point, one can easily determine the required concentration of surfactant by experimentation, with the above figures used as guides.

The reagent may optionally contain a solubilizing agent, which causes both erythrocyte ghosts and mature leukocytes to shrink, thus enabling sharper discrimination of immature cells including hematopoietic progenitor cells. Preferred solubilizing agents are listed below: (1) sarcosine acid derivatives of following general formula or salts thereof:

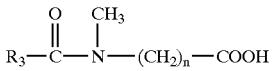

(where $R_3$ is an alkyl group having 10–22 carbon atoms; m is 1–5); (2) cholic acid derivatives of the following general formula:

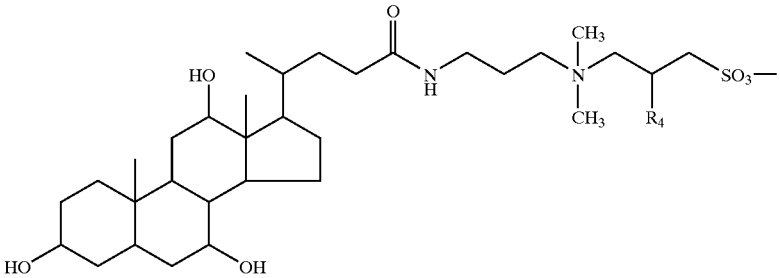

(where R is a hydrogen atom or a hydroxyl group); and (3) methylglucamides of the following general formula:

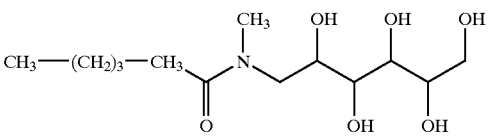

(where y is 5–7).

The preferred concentration of the solubilizing agent ranges from 0.2 to 2.0 g/L if it is a sarcosine acid derivative or salt thereof, 0.1–0.5 g/L in the case of a cholic acid derivative, and 1.0–8.0 g/L in the case of methylglucamide. Specific examples of the preferred solubilizing agent include: sodium N-lauroyl sarcosinate, lauroylmethyl β-alanine sodium salt, lauroyl-sarcosine, CHAPS (3-[(3-cholamidopropyl) dimethylammonio]-1-propanesulfonate), CHAPSO (3-[(3-cholamidopropyl) dimethylammonio]-2-hydroxy-1-propanesulfonate), MEGA8 (octanoyl-N-methylglucamide), MEGA9 (nonanoyl-N-methylglucamide), and MEGA10 (decanoyl-N-methylglucamide). Other useful solubilizing agents include n-octyl β-glucoside, sucrose monocaprate, and N-formylmethylleucylalanine and these may preferably be used at concentrations of 0.01–50.0 g/L.

An amino acid may be incorporated in the reagent under consideration and thus is helpfhl for the purpose of identifying and classifying immature cells including hematopoietic progenitor cells. Any amino acids that are protein constituents may be employed and particularly preferred amino acids are glutamic acid, valine and sulfur-containing amino acids such as methionine, cystine and cysteine. The amino acids may be used in amounts ranging from 1 to 50 g/L, with a preferred range of 8–12 g/L for glutamic acid and 16–24 g/L for methionine.

The reagent may also contain a buffer agent in order to maintain a constant pH, preferably in the range of 5.0–9.0. As long as adjustment to this pH range is possible, any known buffer agents may be used without particular limitations.

If necessary, an osmolarity modifier may be added in order to adjust the osmolarity to be within the range of 150–600 mOsm/kg, preferably 250–380 mOsm/kg.

In case detecting cell information is by supplying a radio-frequency signal at a few MHz and detecting a signal based on the difference between the dielectric constants of corpuscles (also called the RF method), the reagent may be employed with its electrical conductivity adjusted to 3.0–12.0 mS/cm, preferably 6.0–9.0 mS/cm. Suitable for use in the conductivity adjustment are electrolytes including halides, sulfates, nitrates, etc. of alkali metals and alkaline earth metals, for instance, sodium chloride and potassium chloride. There is no need to consider electrical conductivity if cell information is to be obtained by optical means alone, for instance, scattered light.

The method of the invention may be implemented by the following procedure. First, a blood sample is mixed for reaction with the reagent capable of detecting immature cells. Prior to mixing, the blood sample is diluted 100–500 folds, preferably 200–300 folds, with the reagent capable of detecting immature cells. The reaction temperature ranges from 25.0° to 40.0° C., preferably from 30° to 34° C., and the reaction time ranges from 5 to 60 sec, preferably from 10 to 20 sec.

Then, using a particle analyzer, at least one item of cell information is obtained from one cell. Preferably, at least two items of cell information are obtained, for instance, the combination of cell size and cell interior information, or the combination of two pieces of cell interior information. Examples of the cell size information include a signal (DC signal) that are based on the difference between the electrical resistances of two cells that occurs when they pass through an aperture under application of a DC current and low-angle (e.g. 1–6 degrees with the optical axis) scattered light. Examples of the cell interior information include a signal (RF signal), high-angle (8–20 degrees with the optical axis) forward scattered light, lateral (70–110 degrees with the optical axis) scattered light, backward (120–180 degrees) scattered light and the degree of depolarization, all of which are based on the difference between the dielectric constants of two cells that occurs when they pass through the aperture under application of a high-frequency current.

Two types of particle size analyzers are available that can produce more than one item of cell information, one being a known flow cytometer operating on an optical principle and the other being exemplified by models of NE and SE series (both available from Toa Medical Electronics Co., Ltd.) which rely on electrical resistance for operation by adopting the RF/DC detection system. In the RF/DC system, cell size information and cell interior information can be detected simultaneously by superposing a high-frequency signal on a dc current.

Subsequently, a cell distribution profile is constructed on the basis of the data obtained in the previous step. The cell distribution profile is a one-dimensional histogram or, alternatively, a two- or three-dimensional scattergram. A two-dimensional scattergram is preferred.

In order to count HPCs or hematopoietic progenitor cells, a portion of the constructed cell distribution profile has to be delineated as a zone for the appearance of these cells. To this end, one may utilize the CD34 positive nature of the hematopoietic progenitor cells in separating out those hematopoietic progenitor cells by cell separation on the basis of an immunomagnetic bead method and the thus separated cells are assayed with a particle analyzer to confirm the appearance location of the hematopoietic progenitor cells, and this location is designated as an HPC counting zone.

For cell separation, a monocyte-rich sample is first prepared by means of a blood component separator. The sample is then reacted with magnetic beads having an anti-CD34 monoclonal antibody bound thereto (as commercially available under the trademarks DYNABEADS™ of DYNAL A.S.); thereafter, CD34 positive hematopoietic cells are separated with a magnetic cell separator (e.g. Isolex™ of Baxter Co., Ltd.). This is followed by treatment with an enzyme so as to free the CD34 positive cells of the magnetic beads.

The thus prepared sample is mixed with the reagent capable of detecting immature cells and measurements are performed by the RF/DC method using SE-9000 (Toa Medical Electronics Co., Ltd.). The same procedure is applied to a number of samples and the HPC appearance zone is delineated based on the scattergram pattern for the appearance of HPCs.

Once the HPC appearance zone has been delineated in the manner described above, the assay of the actual blood sample is extremely simple and rapid. Stated more specifically, the reagent capable of detecting immature cells is mixed with the blood sample for reaction and cell information is obtained with the particle analyzer to construct a cell distribution profile and the HPCs within the HPC appearance zone are counted. With an apparatus like SE-9000, the steps described above can be carried out by automated IMI channels; hence, it takes only about 1–2 min complete the assay of one blood sample.

The method of the invention can detect at least one of the subclasses of HPCs, i.e., pluripotent stem cells, lymphoid stem cells, CFU-GEMM, BFU-E, CFU-E, CFU-Meg, CFU-GM, CFU-EoS, progenitor B cells and progenitor T cells, among which CFU-GM, CFU-GEMM and CFU-EOS are preferred. These subclasses of HPCs are all CD34 positive cells.

A reagent kit comprising the above-described reagent (capable of detecting immature cells without employing any immunological techniques), for example; a nonionic surfactant; a solubilizing agent; an amino acid and a buffering agent; having a pH of 5.0–9.0, an osmolarity modifier providing an osmolarity of 150–600 mOsm/kg and an electrolyte having an electrical conductivity of 3.0–12.0 mS/cm will detect not only HPCs but also more mature cells including blasts (lymphoblasts and myeloblasts), juvenile granulocytes (promyelocytes, myelocytes and metamyelocytes) and left shifted cells (which usually means the increase in less segmented band neutrophils; however, for the purposes of the invention, this term will refer to band neutrophils per se). These cells may also appear in an HPC containing sample and will be a noise to understanding of the kinetics of HPCs with the aid of the IMI total as in the prior art (see FIG. 2).

In contrast, as is clear from FIG. 3, the effects from these cells can be reduced by counting the number of cells within the zone delineated by the aforementioned method of the invention, providing higher specificity.

Figure 4:
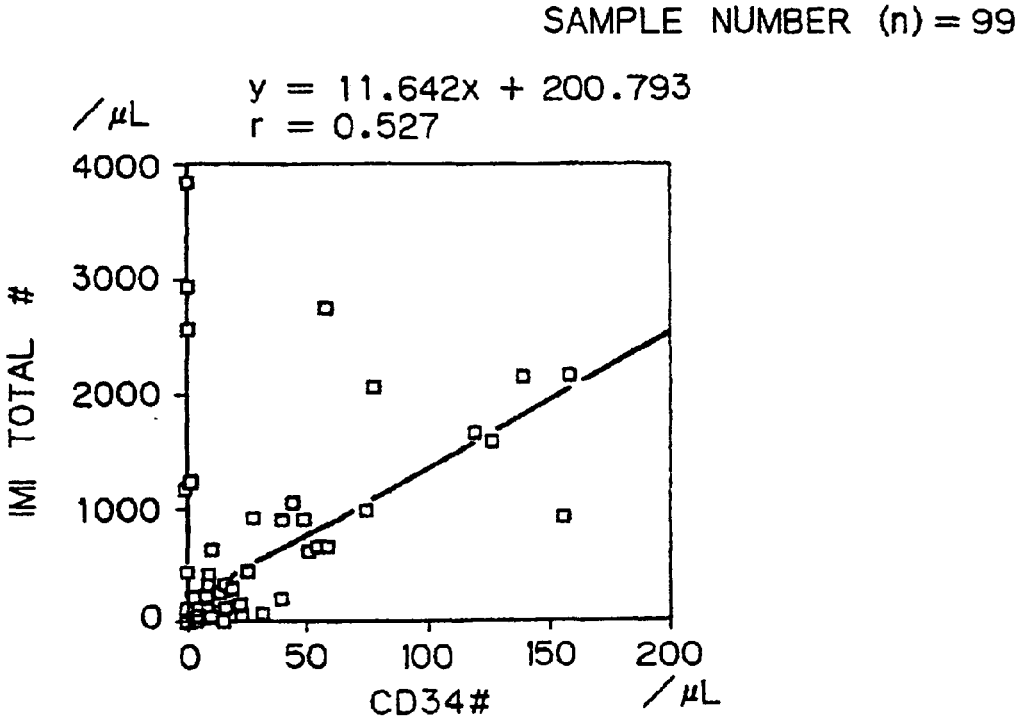
FIG. 4 is a graph showing the correlationship between the IMI total and the CD34 positive cell count.
Figure 5:
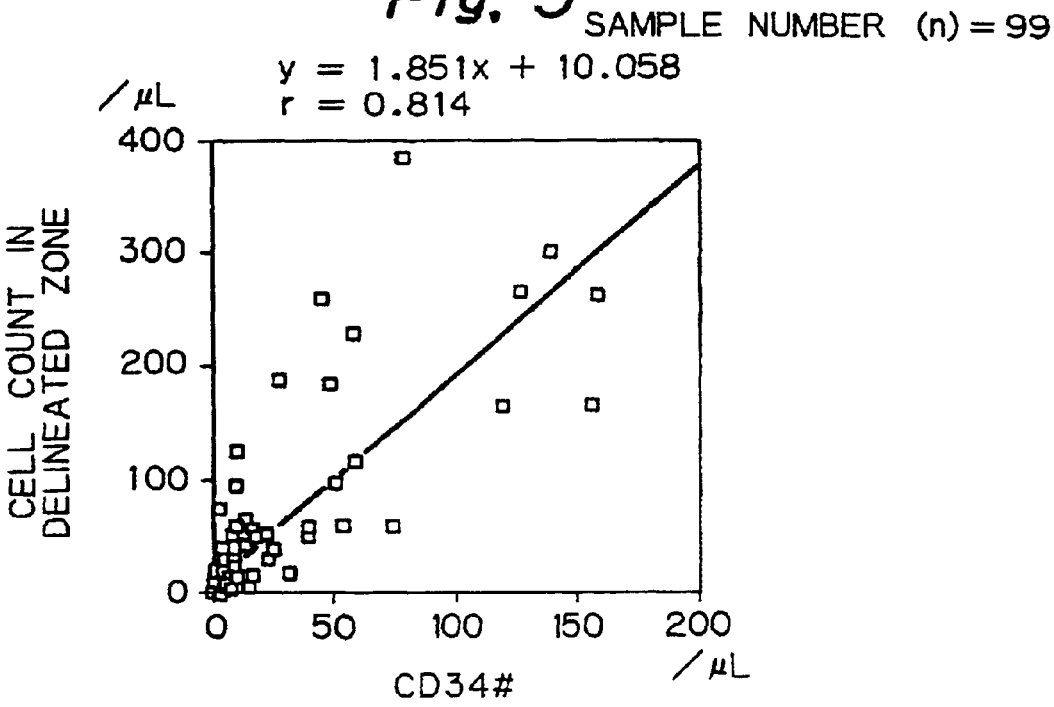
FIG. 5 is a graph showing the correlationship between the CD34 positive cell count and the HPC count as obtained by the method of the invention.

As a result, the HPC count obtained by the method of the invention has a better correlation with the CD34 positive cell count than does the IMI total (compare FIGS. 4 and 5). Typically, but not always, the CD34 positive cell count starts to increase at day 5–7 after the initial administration of a chemical agent prior to the practice of HPC harvest, increases abruptly at day 10–12, then decreases approximately at day 17 and thereafter increases again. This behavior of CD34 positive cell count was monitored more faithfully by the cell count obtained by the invention method than by the IMI total (compare FIGS. 6 and 7). Therefore, the method of the invention is suitable for monitoring the daily changes in the HPCs in the peripheral blood.

Figure 8:
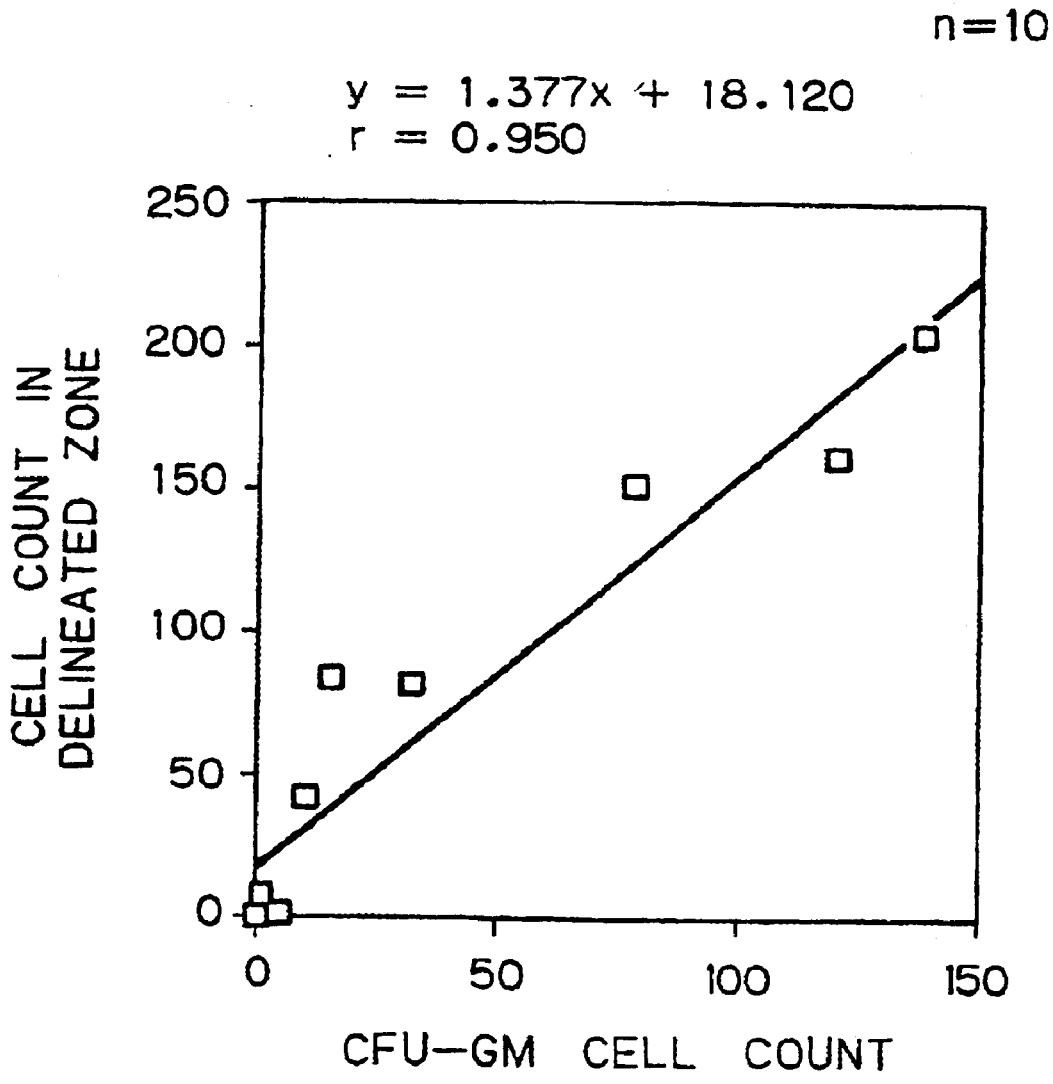
FIG. 8 is a graph showing the correlationship between the HPC count obtained by the method of the invention and the CFU-GM count obtained by the manual method.

The HPC count obtained by the method of the invention was also in good agreement with the number of CFU-GMs which are in a subclass of HPCs (FIG. 8). The practice of PBSCT also involves the administration of hematopoietic drugs such as G-CSF and the invention offers has an additional significant advantage in that it is capable of daily monitoring of the number of CFU-GMs which will appear predominantly as the result of the administration of hematopoietic drugs.

The following examples are provided for the purpose of further illustrating the present invention but are in no way to be taken as limiting.

The reagent capable of detecting immature cells which was used in all of the examples given below had the following formulation:

| (Reagent's formulation) | |
|---|---|
| POE(15) oleyl ether | 5 g |
| Sodium N-lauroyl sarcosinate | 1.5 g |
| Glutamic acid | 10 g |
| Phosphate buffer solution (pH = 7.0; 20 mM) | |
| Sodium chloride | q.s. (for conductivity adjustment to 13.0 mS/cm) |
| purified water | 1 L |

EXAMPLE 1

Delineating HPCs Zone on Scattergram

A monocyte-rich sample was prepared by means of a blood component separator and reacted with magnetic beads having bound thereto an anti-CD34 monoclonal antibody (Becton Dickinson Immunocytometry Systems Co., Ltd.). Thereafter, CD34 positive HPCs were separated by means of a magnetic cell separator (Isolex™ of Baxter Co., Ltd.) and then freed of the magnetic beads by treatment with an enzyme (chymopapain).

The treated sample was mixed with the reagent capable of detecting immature cells (for its formulation, see above) and measurements were conducted on ten samples with an automatic blood cell analyzer (SE-9000 of Toa Medical Electronics Co., Ltd.). On the basis of the pattern for the appearance of HPCs, a zone for their appearance was delineated on the scattergram (FIG. 1).

EXAMPLE 2

Comparing IMI Total with HPC Count

IMI Total Counting

Peripheral blood samples were drawn from patients treated with G-CSF and diluted 250 folds with the reagent capable of detecting immature cells (for its formulation, see above). Following the reaction at 33° C. for 13 sec, measurements were conducted with SE-9000 (Toa Medical Electronics Co., Ltd.) to produce the cell distribution profile shown in FIG. 2. The samples contained not only HPCs but also more differentiated juvenile leukocytes. (See FIG. 2, which shows the distribution ranging from blasts to juvenile cells.) These are included within a population heretofore counted as the IMI total, or the total number of juvenile leukocytes. As already mentioned, the IMI total refers to the sum of the counts within the respective zones for blasts, immature granulocytes and left shifted cells. HPC counting by the method of the invention Samples which were the same as employed in the IMI total counting were subjected to measurements within the zones delineated by the method described in Example 1. The cell distribution profile obtained by these measurements is shown in FIG. 3, from which one can see that by delineating the specific HPC zone, the effect of the cells appearing in the respective zone for blasts, immature granulocytes and left shifts could be sufficiently suppressed to provide a higher specificity.

Example 3

Correlationship with CD34 Positive Cell Count

The IMI total and the HPC count which were obtained by the methods described in Example 2 were checked for their correlationship with the CD34 positive cell count as obtained by flow cytometry using FACScan (Becton Dickinson Immunocytometry Systems Co., Ltd.).

Measurements were conducted on 99 peripheral blood samples to evaluate the correlation between the IMI total and the CD34 positive cell count. The results of the correlation between IMI total and CD34 counts are shown in FIG. 4, (r=0.527).

Similar measurements were conducted to evaluate the correlation between the HPC count by using the specific zone as indicated in Exampl 1 and the CD34 positive cell count. The results of the correlation between HPC count and CD34 counts are shown in FIG. 5, (r=0.814). Thus, the effectiveness of the invention method was demonstrated.

EXAMPLE 4

Correlationship in Daily Changes

Figure 6:
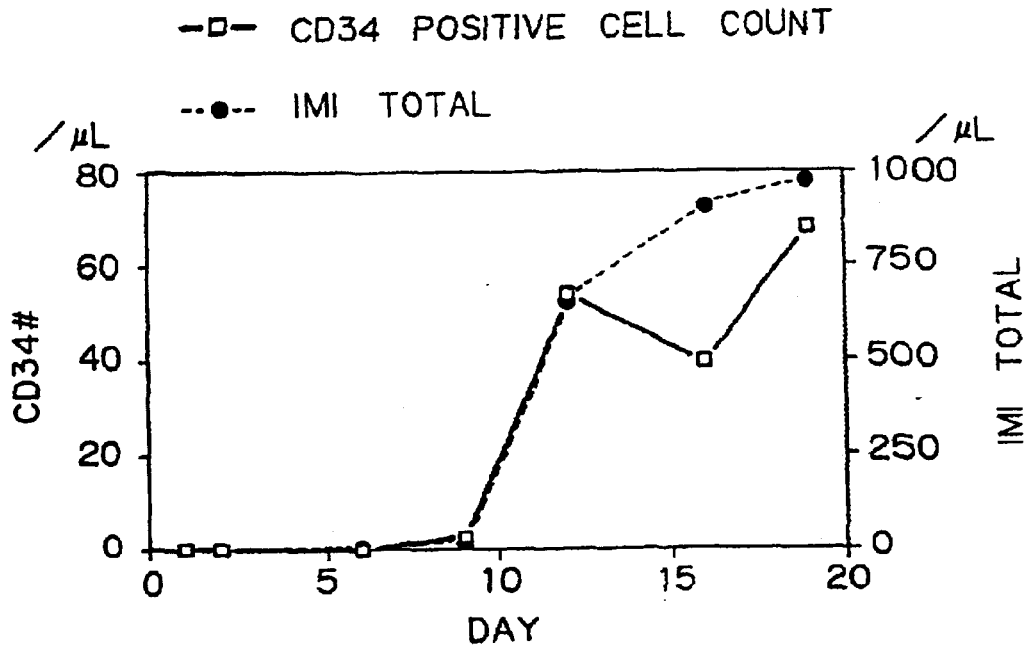
FIG. 6 is a graph showing the daily changes in the CD34 positive cell count and the IMI total.
Figure 7:
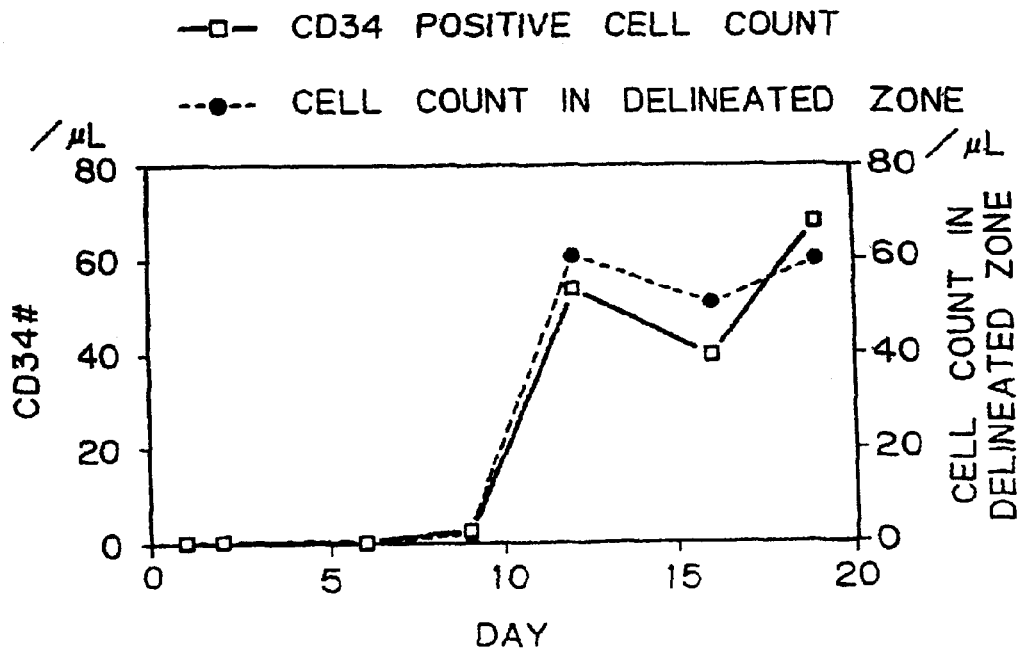
FIG. 7 is a graph comparing the daily change in the CD34 positive cell count with that in the HPC count obtained by the method of the invention.

In this patient, the CD34 positive cell count as obtained by flow cytometry started to increase at day 5–7 after the initial administration of a chemical agent prior to the practice of PBSCT, increased aburptly at day 10–12, then decreased approximately at day 17 and thereafter increased again. This behavior of the CD34 positive cell count was compared with the daily changes in the IMI total and the HPC count that were measured by the methods described in Example 2. The results are shown in FIGS. 6 and 7. FIG. 6 compares the daily change in the CD34 positive cell count with that in the IMI total, and FIG. 7 compares the daily change in the CD34 positive cell count with that in the HPC count in the zone delineated by the method described in Example 1. Obviously, the cell count within the zone delineated by the method of the invention was more accurate than the IMI total in monitoring the change in the CD34 positive cell count, thus providing a more direct representation of the dynamic changes in the CD34 positive cell count.

EXAMPLE 5

Correlationship with CFU-GM Count

The HPC count within the zone delineated by the method described in Example 1 was compared with the count of CFU-GMs in a subclass of HPCs for 10 samples. The CFU-GM count was obtained by the manual method involving colony counting under a microscope. The results of the correlation between the HPC and CFU-GM are shown in FIG. 8, (r=0.950). The samples used in Example 5 were prepared by collecting peripheral blood stem cells after the administration of G-CSF.

The present invention enables HPCs to be detected without employing any immunological techniques but using (1) a reagent capable of detecting immature cells and (2) a particle analyzer which provides the cell information. The invention provides a simple, quick and low-cost method for monitoring the dynamic changes in the HPC count in the peripheral blood and harvested HPC. The conventional colony culture method takes about 2 weeks to complete the assay and even the flow cytometry requires about ≧2 hours. In contrast, the detection method of the invention needs only 1–2 minutes to obtain the result which is a significant advantage over the two conventional techniques. In addition, compared to the method employing the expensive anti-CD34 monoclonal antibody, the method of the invention can be implemented at a very low cost per test; at about one fiftieth of the cost of using the anti-CD34 monoclonal antibody. As further advantages, the method of the invention does not require any sophisticated skill in measurement and, hence, is free from the reproducibility problems that would be caused by different operators.

Further in addition, a zone for the appearance of HPCs is delineated in the method of the invention and this enables the effects of blasts, juvenile granulocytes and band leukocytes to be sufficiently suppressed to accomplish a reliable detection of HPCs.

In PBSCT, a continued, daily measurement for 3–5 days is ideal for monitoring the mobilization of stem cells within the peripheral blood and this can be easily accomplished by adopting the method of the invention. Hence, the invention offers a great benefit to the medical field where PBSCT is replacing BMT as an effective method of treatment of refractory diseases such as leukemia, lymphoma, myeloma, and a number of solid tumors.

What is claimed is:

1. A method for detecting or counting or both detecting and counting hematopoietic progenitor cells, which comprises the steps following:

treating a blood sample with a reagent which detects immature cells without employing any immunological techniques;

obtaining cell information about said treated blood sample using a particle analyzer and constructing a cell distribution profile;

delineating a portion of said profile as a zone in which at least one subclass of hematopoietic progenitor cells appear; wherein said profile zone is delineated through the use of a control sample comprising hematopoietic progenitor cells; and counting the cells within said zone.

2. A method according to claim 1, wherein the cell information consists of two items, one representing cell size and the other representing cell interior.

3. A method according to claim 1, wherein the subclass of hematopoietic progenitor cells is colony forming unit—granulocyte/macrophage; colony forming unit—granulocyte/erythroid/macrophage/megakaryocyte; or colony forming unit—eosinophil.

4. A method according to claim 1, wherein the reagent detects immature cells without employing an immunological techniques is an aqueous solution containing a nonionic surfactant.

5. The method of claim 1, wherein said control sample comprises hematopoietic progenitor cells which have been separated using anti-CD34 antibody.

6. A method according to claim 5, wherein the cell information consists of two items, one representing cell size and the other representing the cell interior.

7. A method according to claim 5, wherein the subclass of hematopoietic progenitor cells is colony forming unit—granulocyte/macrophage; colony forming unit—granulocyte/erythroid/macrophage/megakaryocyte; or colony forming unit—eosinophil.

8. A method according to claim 5, wherein the reagent detects immature cells without employing any immunological techniques is an aqueous solution containing a nonionic surfactant.

*9. A method according to claim 1, wherein the particle analyzer is an optical particle analyzer.*

*10. A method according to claim 9, wherein the particle analyzer comprises a flow cytometer.*

*11. A method according to claim 1, wherein the particle analyzer uses an electrical resistance method.*

*12. A method according to claim 11, wherein the particle analyzer comprises a RF/DC detection system.*

* * * * *